(12) United States Patent
Roberts et al.

(10) Patent No.: US 12,343,026 B2
(45) Date of Patent: Jul. 1, 2025

(54) DEVICE, SYSTEMS, AND METHODS FOR TREATING A KIDNEY STONE

(71) Applicant: The Regents of the University of Michigan, Ann Arbor, MI (US)

(72) Inventors: William W. Roberts, Ann Arbor, MI (US); Timothy L. Hall, Ann Arbor, MI (US); Ali H. Aldoukhi, Ann Arbor, MI (US); Khurshid R. Ghani, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 913 days.

(21) Appl. No.: 16/981,174

(22) PCT Filed: Mar. 14, 2019

(86) PCT No.: PCT/US2019/022317
§ 371 (c)(1),
(2) Date: Sep. 15, 2020

(87) PCT Pub. No.: WO2019/178387
PCT Pub. Date: Sep. 19, 2019

(65) Prior Publication Data
US 2021/0015507 A1    Jan. 21, 2021

Related U.S. Application Data

(60) Provisional application No. 62/643,811, filed on Mar. 16, 2018.

(51) Int. Cl.
*A61B 17/221* (2006.01)
*A61B 18/26* (2006.01)
(Continued)

(52) U.S. Cl.
CPC ............ *A61B 17/221* (2013.01); *A61B 18/26* (2013.01); *A61B 1/307* (2013.01);
(Continued)

(58) Field of Classification Search
CPC ....... A61B 17/221; A61B 18/26; A61B 1/307; A61B 2017/22079; A61B 2017/2215;
(Continued)

(56) References Cited

U.S. PATENT DOCUMENTS

| | | | |
|---|---|---|---|
| 8,430,826 B2 * | 4/2013 | Uznanski | A61B 90/96 600/565 |
| 8,751,018 B1 * | 6/2014 | Sethna | A61N 1/05 607/119 |

(Continued)

OTHER PUBLICATIONS

International Search Report and Written Opinion for PCT/US19/22317. Mailed Jun. 6, 2019. 12 pages.
(Continued)

*Primary Examiner* — Scott M. Getzow
(74) *Attorney, Agent, or Firm* — Casimir Jones, S.C.; Tanya A. Arenson

(57) ABSTRACT

Provided herein are devices, systems, and methods for treating a kidney stone. In particular, provided herein are suction devices, laser systems, and related methods for use in treating a kidney stone.

5 Claims, 15 Drawing Sheets

(51) Int. Cl.
    *A61B 1/307* (2006.01)
    *A61B 17/22* (2006.01)
    *A61B 18/00* (2006.01)
(52) U.S. Cl.
    CPC ............... *A61B 2017/22038* (2013.01); *A61B 2017/22079* (2013.01); *A61B 2017/2215* (2013.01); *A61B 2018/00511* (2013.01); *A61B 2018/00577* (2013.01); *A61B 2018/00982* (2013.01); *A61B 2218/007* (2013.01)
(58) Field of Classification Search
    CPC   A61B 2018/00511; A61B 2018/00577; A61B 2018/00982; A61B 2218/007
    See application file for complete search history.

(56) References Cited

U.S. PATENT DOCUMENTS

| | | | |
|---|---|---|---|
| 9,629,529 | B1 | 4/2017 | Idovina et al. |
| 2002/0082470 | A1 | 6/2002 | Devries et al. |
| 2007/0027357 | A1* | 2/2007 | Bertolero ........... A61B 17/0206 600/37 |
| 2009/0287193 | A1 | 11/2009 | Desai et al. |
| 2011/0152855 | A1* | 6/2011 | Mayse ................. A61B 18/18 606/33 |
| 2013/0172828 | A1* | 7/2013 | Kappel .......... A61B 17/320016 606/174 |
| 2013/0296902 | A1 | 11/2013 | Vonderwalde et al. |
| 2016/0030070 | A1* | 2/2016 | Esiner ................... A61M 1/77 606/115 |

OTHER PUBLICATIONS

Lange et al., Stone/tissue differentiation during intracorporeal lithotripsy using diffuse white light reflectance spectroscopy: In vitro and clinical measurements. Lasers Surg Med. Oct. 2014;46(8):614-9.

Lange et al., Stone/tissue differentiation for holmium laser lithotripsy using autofluorescence. Lasers Surg Med. Nov. 2015;47(9):737-44.

* cited by examiner

A

B

C

D

A

B

A

B

A

Ureteral Access Sheath

B

C

D

A

B

A

B

C

A

B

DEVICE, SYSTEMS, AND METHODS FOR TREATING A KIDNEY STONE

CROSS-REFERENCE TO RELATED APPLICATION

This patent application is a national phase application under 35 U.S.C. § 371 of PCT International Application No. PCT/US2019/022317, filed Mar. 14, 2019, which claims the benefit under 35 U.S.C. § 119 to U.S. Provisional Patent Application No. 62/643,811, filed on Mar. 16, 2018, the entirety of which is incorporated herein by reference.

FIELD

Provided herein are devices, systems, and methods for treating a kidney stone. In particular, provided herein are suction devices, laser systems, and related methods for use in treating a kidney stone.

BACKGROUND

Kidney stone disease, also known as urolithiasis, is characterized by the presentation of a solid piece of material (known as a calculus or kidney stone) in the urinary tract. Kidney stones typically form in the kidney and leave the body in the urine stream. A small stone may pass without causing symptoms. If a stone grows to more than 5 millimeters (0.2 in), it can cause blockage of the ureter resulting in severe pain in the lower back or abdomen. A stone may also result in blood in the urine, vomiting, or painful urination. About half of people who experience a kidney stone will have another stone within ten years.

Treatments for kidney stones include medical expulsive therapy (e.g., using alpha adrenergic blockers (such as tamsulosin) or calcium channel blockers (such as nifedipine)), extracorporeal shock wave lithotripsy (ESWL), ureteroscopic surgery, and percutaneous nephrolithotomy surgical procedures.

In some surgical procedures, a laser may be used to ablate the kidney stone. Conventionally, the laser breaks the stone into stone fragments, often up to 4 mm size, which must be manually extracted. New developments in laser technology allow for stone "dusting" rather than just fragmentation. This technique erodes stones and produces sand particles less than 0.5 mm. Even with these recent developments, it is challenging to remove all stones and fragments, in part, because dusting creates a cloud of particles, through which remaining stones and fragments are difficult to visualize. Recent work has demonstrated that even with meticulous technique, the stone free rate following ureteroscopy is only about 55-69% due to residual fragments that are inadvertently left behind. Patients experience better outcomes and fewer future stone events when all stone fragments are removed. Accordingly, a need exists for improved stone extraction techniques that more thoroughly, accurately, and efficiently remove stone fragments.

A need also exists for more efficient treatment of renal calculi that allows for outpatient ureteroscopic treatment of stones greater than 20 mm, rather than more invasive inpatient percutaneous nephrolithotomy techniques which have greater risk and higher morbidity.

SUMMARY

Provided herein are embodiments of suction devices for use in fragmenting and removing kidney stones. In some embodiments, the device is used during ureteroscopic laser lithotripsy to improve treatment of renal and ureteral stones in several ways. For example, in some embodiments, the device facilitates stabilization of the stone which allows a greater proportion of laser pulses to strike the stone, compared to conventional techniques. This shortens lasing time and markedly decreases time spent navigating the ureteroscope to identify and target stones and stone fragments. In some embodiments, the device minimizes retropulsion of stone debris (stone fragments and small particles) that can escape into other portions of the kidney collecting system and ureter. This is accomplished, at least in part, due to one or more of the following features: the device includes a bended shape that allows for positioning of the suction device on a side of a stone directly opposing the laser beam; the device includes a conical shape, which constrains fragments in the vicinity of the suction outflow and prevents escape of fragments away from the laser treatment zone; and the suction from the exit hole of the device holds small fragments within the target zone of the laser and allows particles less than 1 mm in size (e.g., diameter) to be evacuated through the suction tube and out of the body. This produces better and more efficient clearance of stone and higher stone free rates.

In some exemplary embodiments, the device as described herein is inserted into the ureter or through an access sheath up into the pelvis of the kidney. The suction tubing at the tapered end of the device passes down through the ureter or access sheath and out of the body to a suction pump or other source of suction. In some embodiments, the device is designed so that it is inserted in a collapsed position, and then once in the kidney pelvis, is expanded/unfurled to an open position. In some embodiments, to use the device, a conventional ureteroscope is inserted into the kidney and navigated through all calyces to identify the stone burden. The stone suction device may be inserted through a ureteral access sheath, external to a ureteral access sheath, or through a percutaneous access tract. Stones are manipulated to a distal opening of the stone suction device and placed inside. During laser treatment, the ureteroscope is also positioned at the distal opening of the stone suction device with stones positioned between the ureteroscope and the proximal end of the stone suction device. A laser fiber is inserted through the ureteroscope and positioned on an opposing side of the stone relative to the suction device. Irrigation inflow is provided through the working channel of the ureteroscope. In some embodiments, the suction from a proximal end of the stone suction device is initiated such that the rate of outflow of fluid approximately matches the rate of inflow of fluid through the ureteroscope. Laser lithotripsy or other desired treatment is then performed within the suction cone with, in at least certain examples, one or more of the advantages as described above.

Data obtained during the course of development of embodiments of the present disclosure demonstrated marked improvement of stone fragmentation and clearance rates using the stone suction device with suction compared to without suction.

For example, in some embodiments provided herein is a device, comprising suction tubing having or configured to have a bend of greater than 90 degrees in a distal portion of the suction tubing; and a suction cone comprising an opening at a proximal end, wherein the opening is operably linked to the suction tubing, and the suction cone further includes a suction cone body comprising a distal opening, wherein the distal opening has a larger diameter than the proximal opening. In some embodiments, the distal opening has a diameter of 4-12 mm (e.g., 6-10, 7-10, 7.5, or 10 mm). In some embodiments, the proximal opening has a diameter of 0.5 to 1.5 mm (e.g., 1.0 mm). In some embodiments, the device comprises a rounded proximal region adjacent the proximal opening, wherein the proximal region has a smaller outer diameter than the suction cone. In some embodiments, the device is deployable between a collapsed configuration and an expanded configuration. In some embodiments, the device further comprises one or more control wires configured for deploying the suction cone into the expanded configuration. In some embodiments, the suction cone is constructed of a flexible material (e.g. including but not limited to, a polymer, nickel titanium, or a wire mesh). In some embodiments, the control wire is a nickel titanium wire. In some embodiments, when the device is in the expanded configuration, the suction tubing is oriented in a curved configuration. In some embodiments, the suction tubing extends from the proximal opening of the suction cone and makes a turn (or otherwise includes a bend) greater than 90 degrees (e.g., greater than 90 and less than or equal to 180 degrees (e.g., 100, 110, 120, 130, 140, 150, 160, 170, or 180 degrees)) when the suction cone is in a deployed configuration. In some embodiments, the control wires are attached to a handle.

Further embodiments provide a system, comprising a device as described herein; and a suction pump. In some embodiments, the system further comprises one or more of a ureteroscope, a ureter access sheath, or a laser fiber.

Yet other embodiments provide a method of ablating, or otherwise fragmenting or dusting, a renal calculus (also called a kidney stone), and removing the ablated renal calculus. The method may comprise one or more of the following steps: a) placing a laser on a first side of a renal calculus and in proximity to the renal calculus; placing a device having a suction cone as described herein on a second side of the renal calculus and in proximity to the renal calculus; b) expanding the device to a deployed configuration (in embodiments that require expansion); c) firing the laser toward the renal calculus to fragment the renal calculus; and d) applying suction using a suction pump or other suction mechanism, such that the renal calculus or fragments thereof are captured in the suction cone. In some embodiments, the method further comprises the step of e) removing the renal calculus or fragments thereof through the tubing of the device. In some embodiments, the first side of the renal calculus and the second side of the renal calculus are opposing sides. In some embodiments, the laser is passed through a ureteral access sheath to reach the renal calculus. In some embodiments, the device is advanced through the ureteral access sheath, external to the ureteral access sheath, or through an inner cannula in the ureteral access sheath. In some embodiments, the device is passed over a guide wire in a ureter. In some embodiments, the device is inserted through a percutaneous access tract (e.g., the device is not passed through the ureter). In some embodiments, the laser is a component of a ureteroscope. In some embodiments, the device is advanced in an undeployed configuration and deployed at the site of the renal calculus. In some embodiments, fluid is infused to the site of the renal calculus during ablation/fragmentation/dusting.

Additional embodiments provided herein are directed to improved lithotripsy laser systems and methods of use.

Additional embodiments are described herein.

DESCRIPTION OF THE DRAWINGS

FIGS. 1A-B respectively show graphs of A) time vs. reflectance change and B) time vs. distance, from laser firings, as explained in Example 2 below.

DESCRIPTION

Ureteroscopic holmium laser lithotripsy is now a dominant modality for treatment of ureteral and renal stones. Whether stones are fragmented or dusted, retropulsion of stone away from the laser target zone may become more pronounced as the residual mass of the stone decreases. Much time and energy can be spent re-localizing, targeting, and treating/extracting small residual stone fragments. In order to address this issue or other issues associated with treatment of ureteral and renal stones, the present disclosure provides improved devices and methods for laser lithotripsy or other modalities for fragmenting or dusting stones. In embodiments, devices and methods of the present disclosure provide one or more of the following features: suction stabilization to "hold" stone fragments within the target zone of the laser fiber; simultaneous evacuation of small stone fragments; and containment of stone fragments in a conical chamber to rapidly facilitate re-engagement with suction if the stones should be dislodged from the target zone during laser lithotripsy.

Figure 1:
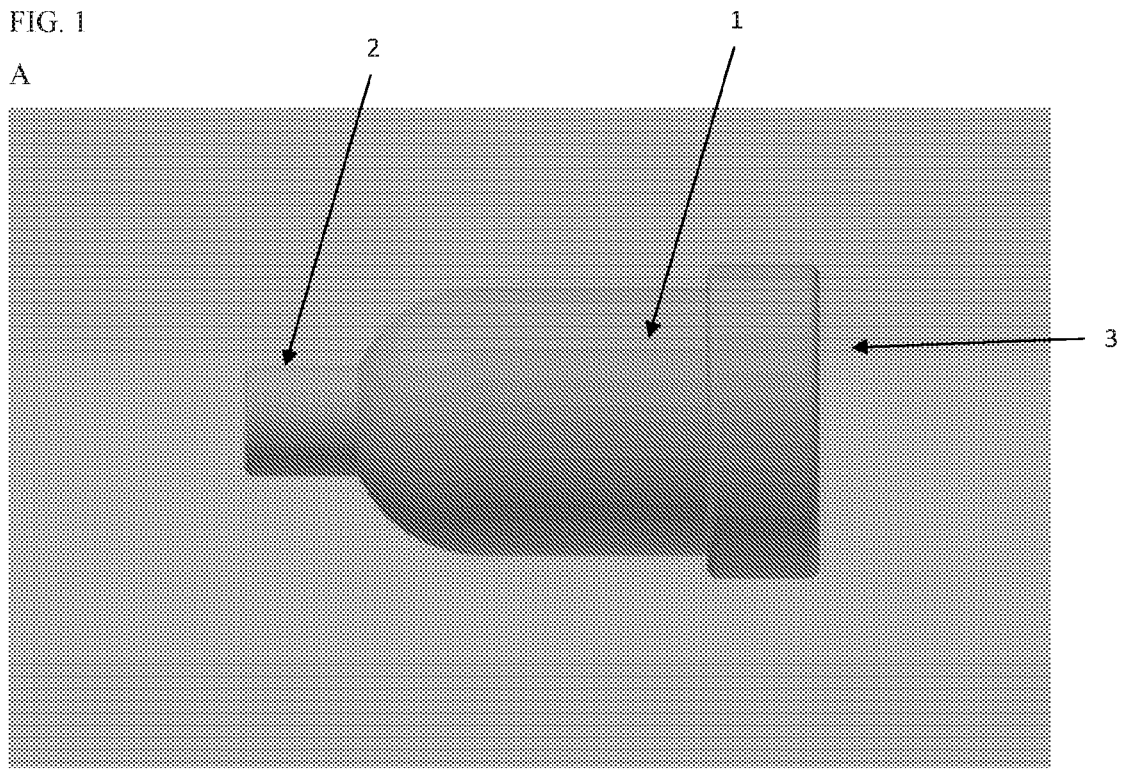
FIGS. 1A-D respectively show A) a side view of one embodiment of a suction cone in a deployed configuration; B) a distal view of the embodiment of the suction cone in the deployed configuration; C) a perspective view of the embodiment of the suction cone in the deployed configuration; and D) an isometric view of at least a portion of the embodiment of the suction cone.
Figure 1:
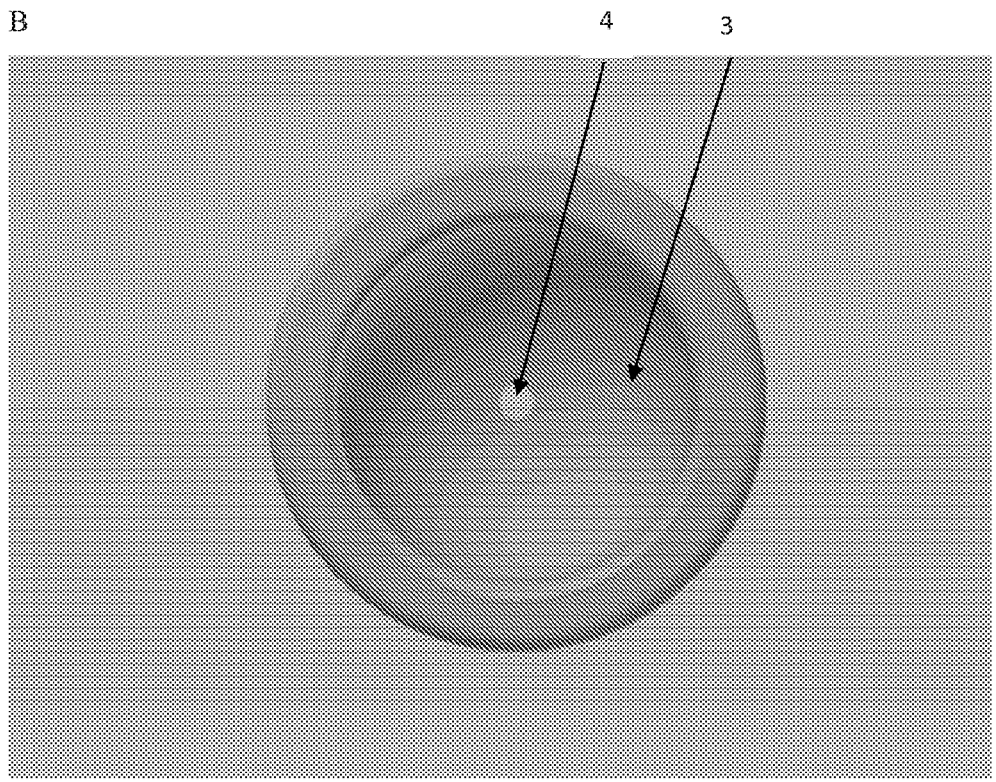
Figure 1:
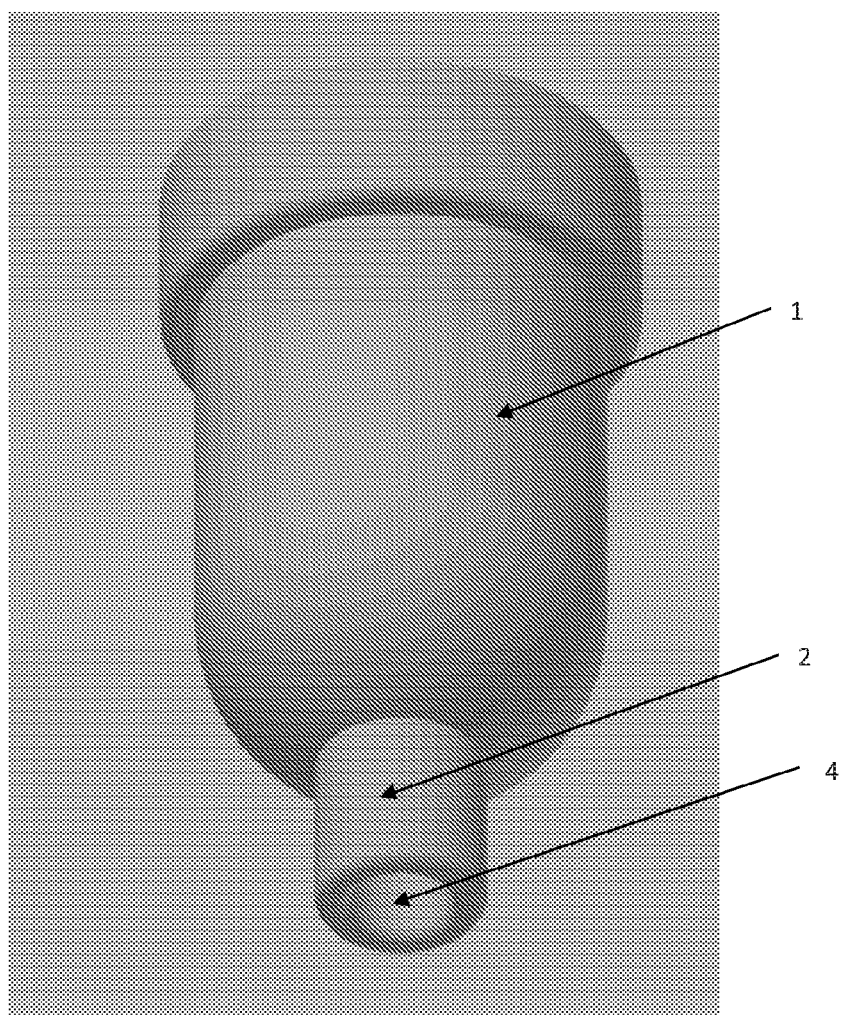
Figure 1:
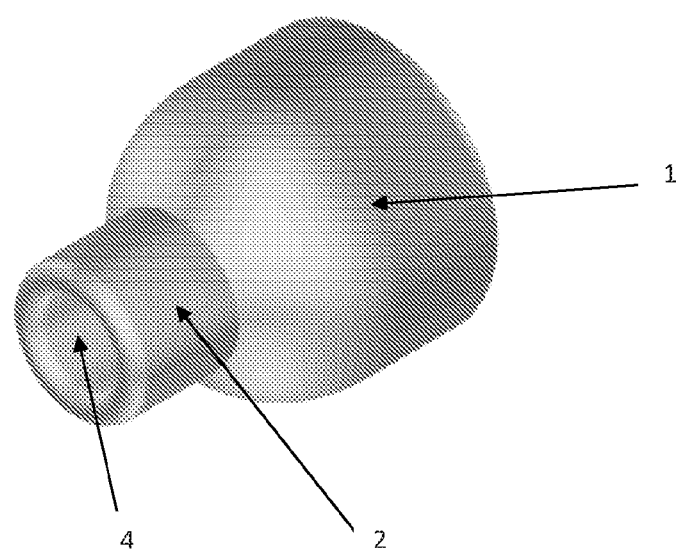

Accordingly, in some embodiments, provided herein is a suction device comprising a suction cone coupled to suction tubing. Referring to FIGS. 1A-D, the cone is described in more detail. Referring to FIG. 1A, shown is a suction cone in a side view. Still referring to FIG. 1A, shown is suction cone body 1, distal opening 3, and proximal region 2. Now referring to FIG. 1B, shown is a distal view showing distal opening 3 and proximal opening 4. Now referring to FIG. 1C, shown is a perspective view of the suction cone showing suction cone body 1, proximal region 2 (e.g., cylindrical tubing), and proximal opening 4. Now referring to FIG. 1D, shown is an isometric view of the suction cone showing suction cone body 1, proximal region 2, and proximal opening 4.

In some embodiments, the suction cone is an expandable/collapsible cone formed of a flexible material. The flexible material may be any suitable biocompatible material or combination of materials, including but not limited to, polyethylene or one or more other polymers, a nickel titanium (nitinol), or other wire mesh. In the expanded configuration, the distal opening 3 of the cone is 4-12 mm (e.g., 6-10, 7-10, 7.5, or 10 mm) in diameter. A smaller opening at the proximal end of the cone (e.g. proximal opening 4) is attached to non-collapsible suction tubing. In some embodiments, the smaller opening has a diameter of 1 mm (e.g., 0.5 to 1.5 mm). Cone body 1 tapers from distal opening 3 (or a point on cone body proximal to distal opening 3) to the distal end of proximal region 2.

Figure 2:
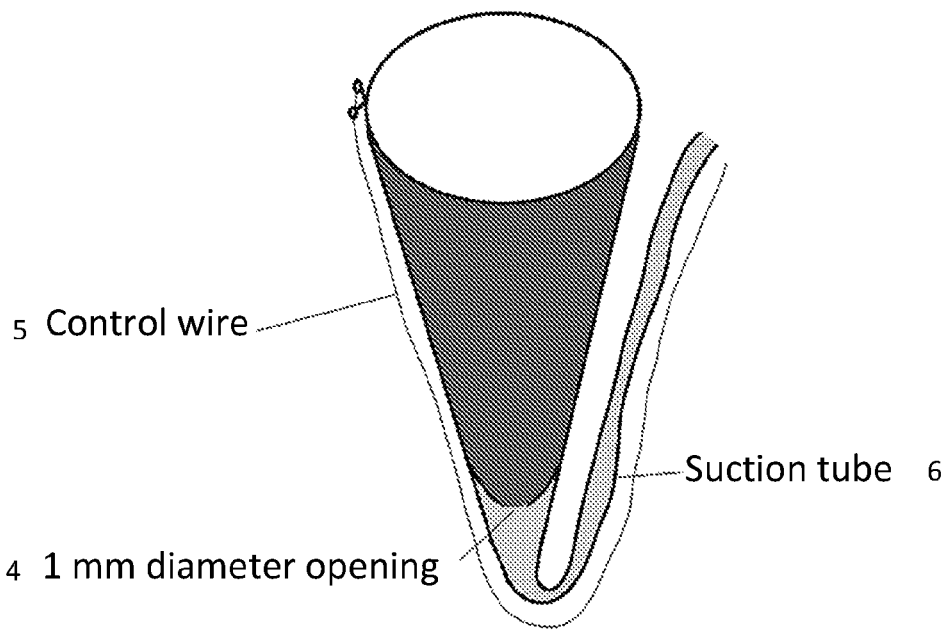
FIGS. 2A-B respectively show A) a schematic view of another embodiment of a suction cone and suction tubing, wherein the suction cone includes a control wire for deploying the suction cone into an expanded configuration and B) a schematic view of a further embodiment of a suction cone and suction tubing, wherein the suction cone includes a control wire for deploying the suction cone into an expanded configuration and a nitinol wire.
Figure 2:
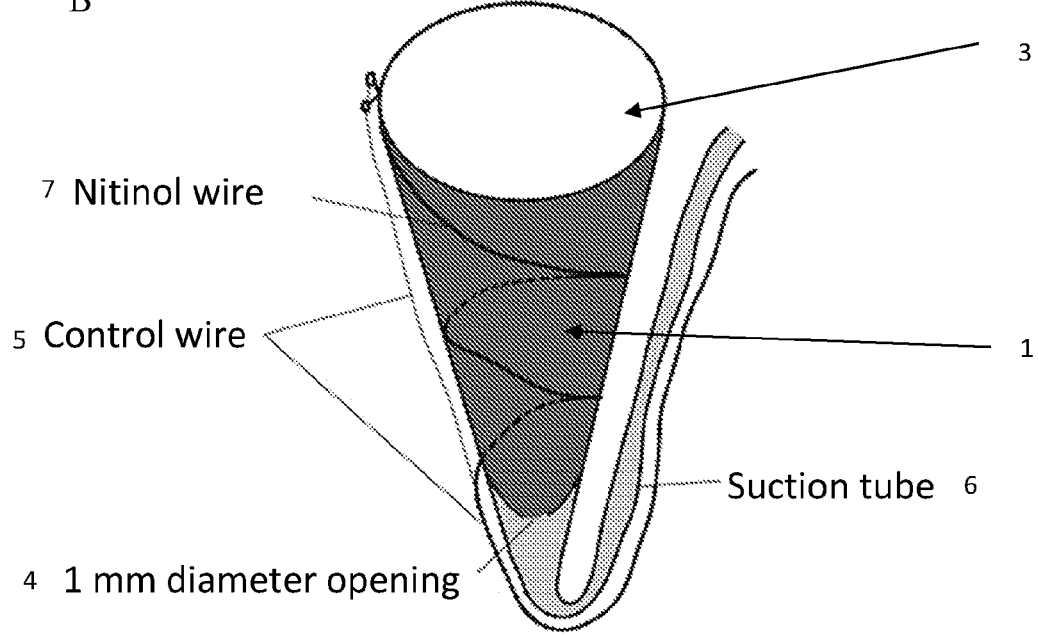

Now referring to FIG. 2A, shown is a suction cone with suction tube 6 and control wire 5. Now referring to FIG. 2B, shown is further configuration of a suction cone with suction tube 6, control wire 5, and additional guide wire 7 (shown as nitinol in FIG. 2B but not limited to nitinol). Control wire 5 may also be referred to as a guidewire.

Figure 3:
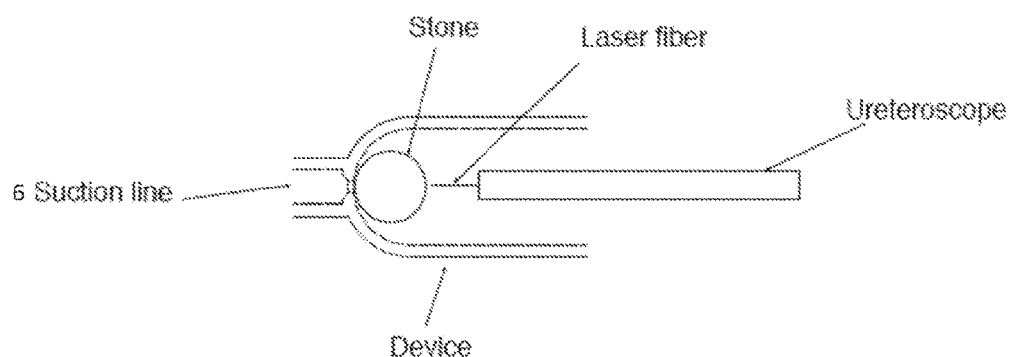
FIGS. 3A-B respectively show A) a schematic drawing depicting the positioning of an embodiment of a suction device and a laser fiber relative to a stone; and B) a schematic view of an embodiment of a suction cone showing a guide wire and eyelet in the device.
Figure 3:
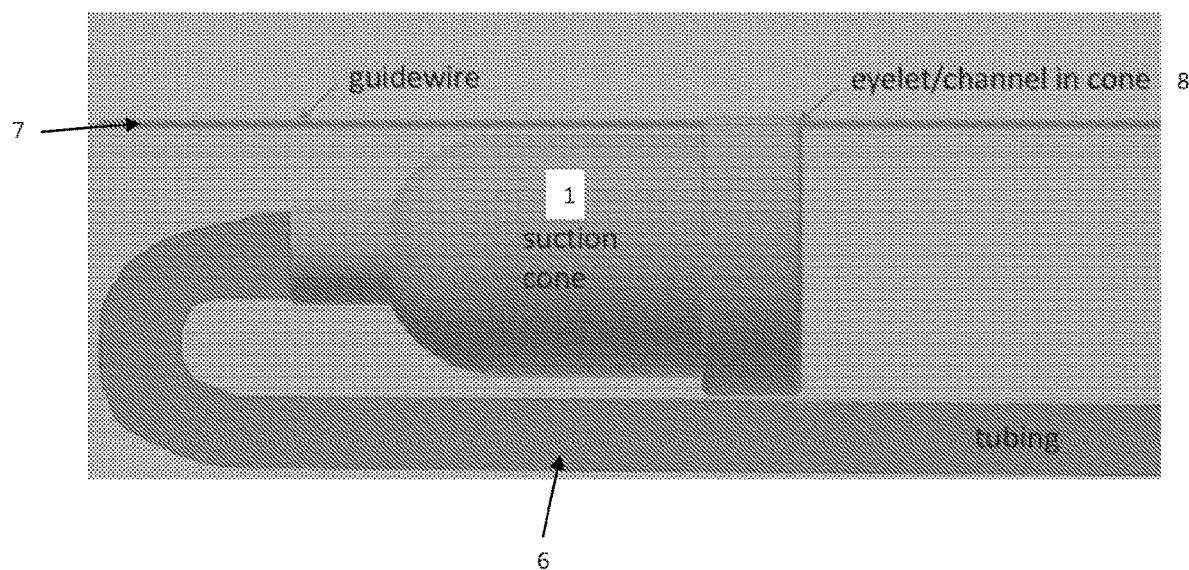

Now referring to FIG. 3, shown is a schematic of a suction cone and the distal end of a suction tube placed in the proximity of a kidney stone. At least in a deployed configuration, the suction tubing is oriented in a curved "candy cane" configuration that allows the ureteroscope to directly advance into the large opening of the cone upon advancement from the ureter into the renal pelvis. In various embodiments, the suction tubing extends from the proximal end of the cone, makes a turn, or bend, greater than 90 degrees, and passes down the ureter to the outside of the body. In some embodiments, the curve/bend is greater than 100 degrees, 110 degrees, 120 degrees, 130 degrees, 140 degrees, or 150 degrees. In some embodiments, the curve has a bend equal to or approximately equal to 180 degree. In some embodiments, the proximal end of the suction tubing is attached to a suction pump outside of the body, or to any other source of suction, which controls suction through the suction tubing.

FIG. 3B shows a device with suction line 6 and guide wire 5. Still referring to FIG. 3B, shown is guide wire 5 passing through an eyelet or channel 8 in the suction cone body 1. In at least some embodiments, one or more control wires or guidewires also may extend with the suction tubing from the cone body 1 to the outside of the patient's body. In some embodiments, the one or more control wires are one or more nitinol control wires. In some embodiments, the one or more control wires are positioned within the lumen of the suction tubing, in the patient's body, or along an exterior of the suction tubing. In some embodiments, the proximal end of the one or more control wires couple to a handle; manipulation of the one or more control wires via the handle allows opening and closing of the suction cone (e.g., to deploy the suction cone to its deployed configuration). For example, as shown in FIG. 2B, a nitinol wire 7 may wrap around or within body 1, with wire 7 being biased in an expanded configuration shown in FIG. 2B. Body 1 and wire 7 may have a contracted/collapsed configuration during insertion in the body, and then assume the expanded configuration upon positioned distal to a kidney stone, for example, by releasing a restraining force from body 1 and wire 7.

Figure 4:
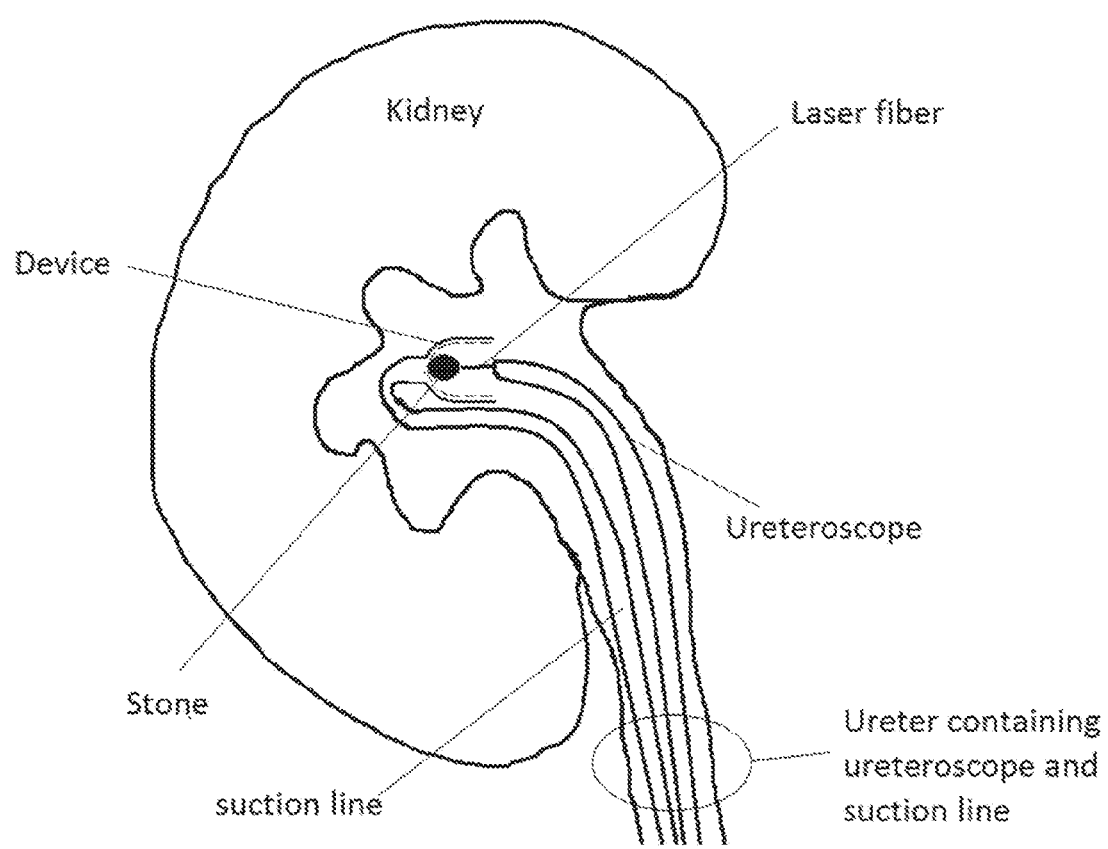
FIG. 4 shows a schematic drawing depicting an exemplary placement of an embodiment of a suction device, laser fiber, and ureteroscope within the anatomy of a patient.

Now referring to FIG. 4, in use, in some embodiments, the suction tubing and suction cone are advanced through the lumen of a standard ureteral access sheath (see FIGS. 5A-5D) to reach the kidney. In some embodiments, the suction tubing and suction cone pass through the ureter external to the ureteral access sheath. In some embodiments, the suction tubing is incorporated into a specially designed ureteral access sheath. In such an embodiment, the suction cone (e.g., in its collapsed configuration) is advanced as a payload within a specially designed inner cannula. In some embodiments, no access sheath is used. In such an embodiment, the suction cone (e.g., in the collapsed configuration) is passed over a guide wire into the renal pelvis. The ureteroscope may be passed over a second wire alongside the suction tubing into the renal pelvis, or the same wire.

In some embodiments, the narrowed, distal and/or proximal end of the suction cone is rounded (e.g., with rounded edges or a bullet-shaped design) to facilitate advancement and positioning.

In some alternative embodiments, the suction cone is inserted through a percutaneous access tract into the collecting system. In this configuration, the suction tubing projects straight from the tapered end of the cone, without the approximately 180 degree bend shown in FIG. 3B, for example.

In the various embodiments, the suction system is configured such that, when deployed in the body, the opening of the suction cone is positioned directly opposite the laser beam, relative to the stone (as shown in FIG. 3A). Advantageously, such a configuration minimizes the retropulsion and dispersion of stone fragments within the body, providing instead for focused stone targeting that directs stone fragments directly into the suction cone and tubing.

In some alternative embodiments, the suction cone is advanced through the outer guide sheath and positioned without the use of a guidewire. In such embodiments, the suction cone may not have an eyelet or channel for receiving a guidewire.

Figure 6:
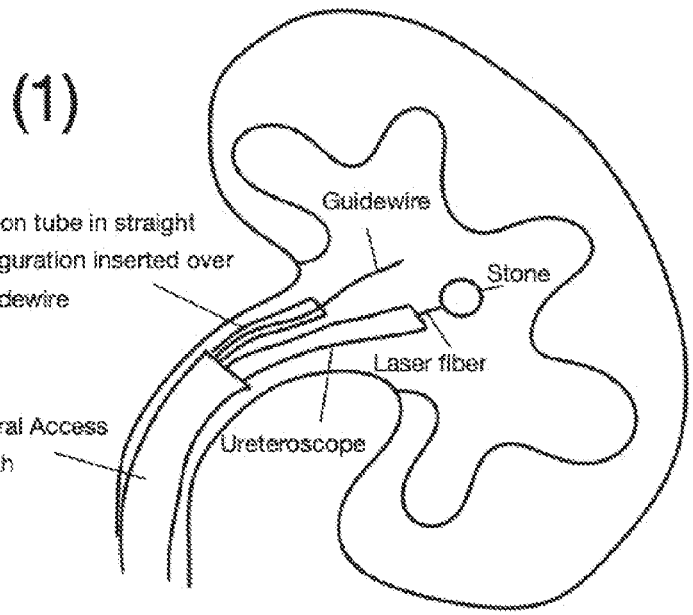
FIG. 6 shows schematic drawings of an exemplary system and method in which the suction tube is formed of a shape memory material and the suction cone and suction tubing are passed over the guidewire.
Figure 6:
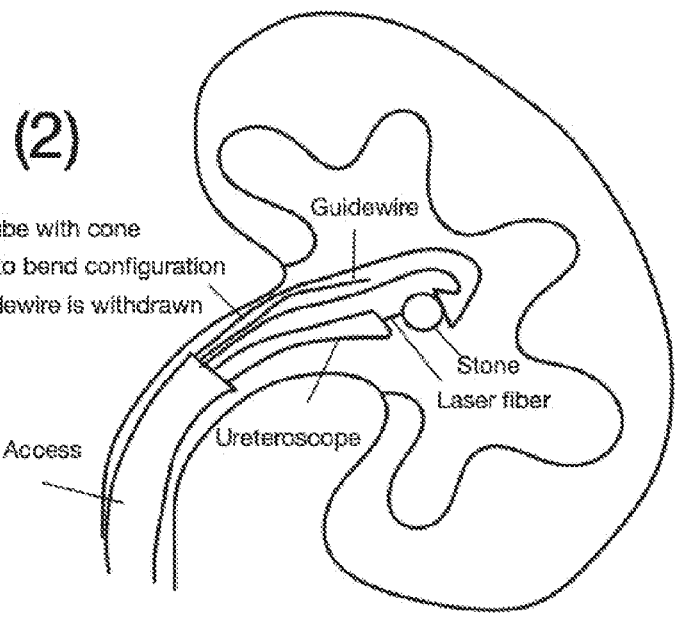

Now referring to FIG. 6, in some embodiments, the suction device includes a suction cone and suction tubing pre-formed with a bend. In some embodiments, at least the pre-bent portion of the suction tubing is formed with a shape memory material. In such embodiments, the device is flexible enough that it straightens over the guidewire and only deforms back to the bent configuration when advanced beyond the guidewire.

In some embodiments, the suction tubing includes one or more pullwires positioned within the lumen or body of the tubing. The pullwires extend from a distal portion of the tubing to beyond the proximal end of the tubing and are configured such that pulling on the one or more wires creates tension in the distal portion of the tubing and induces a bend.

Figure 5:
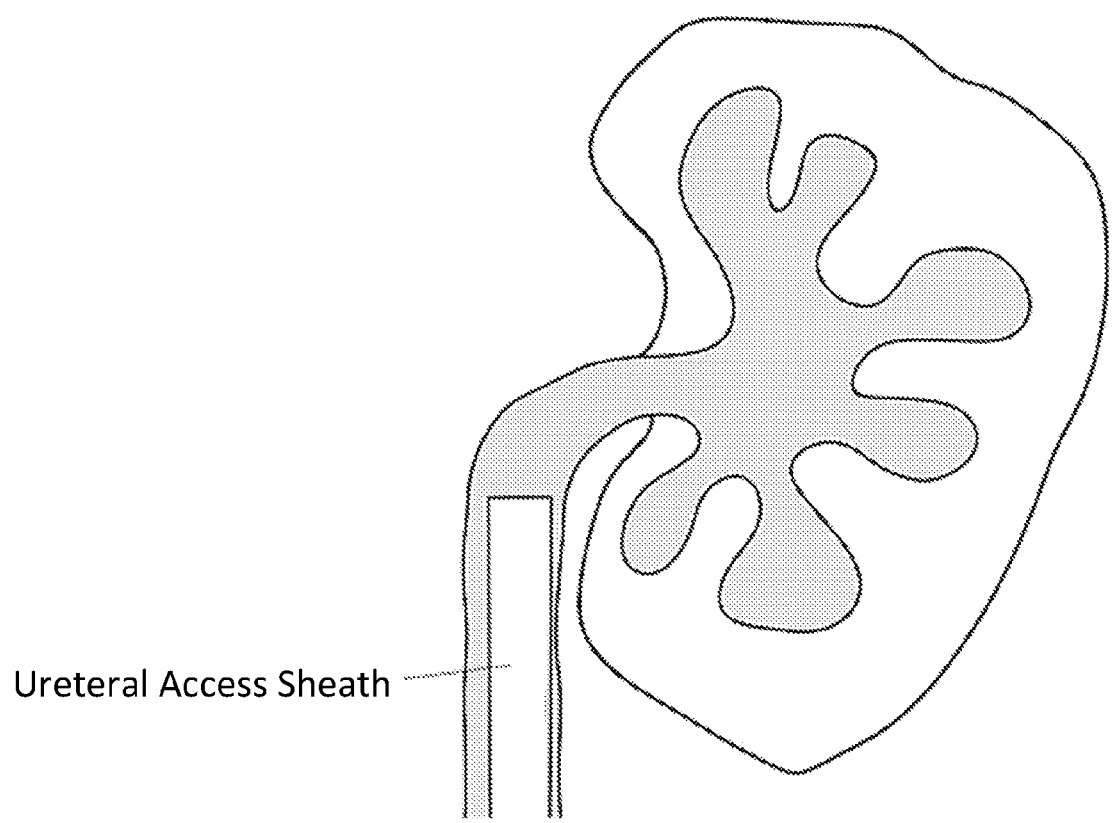
FIGS. 5A-D show a schematic of an exemplary device in use.
Figure 5:
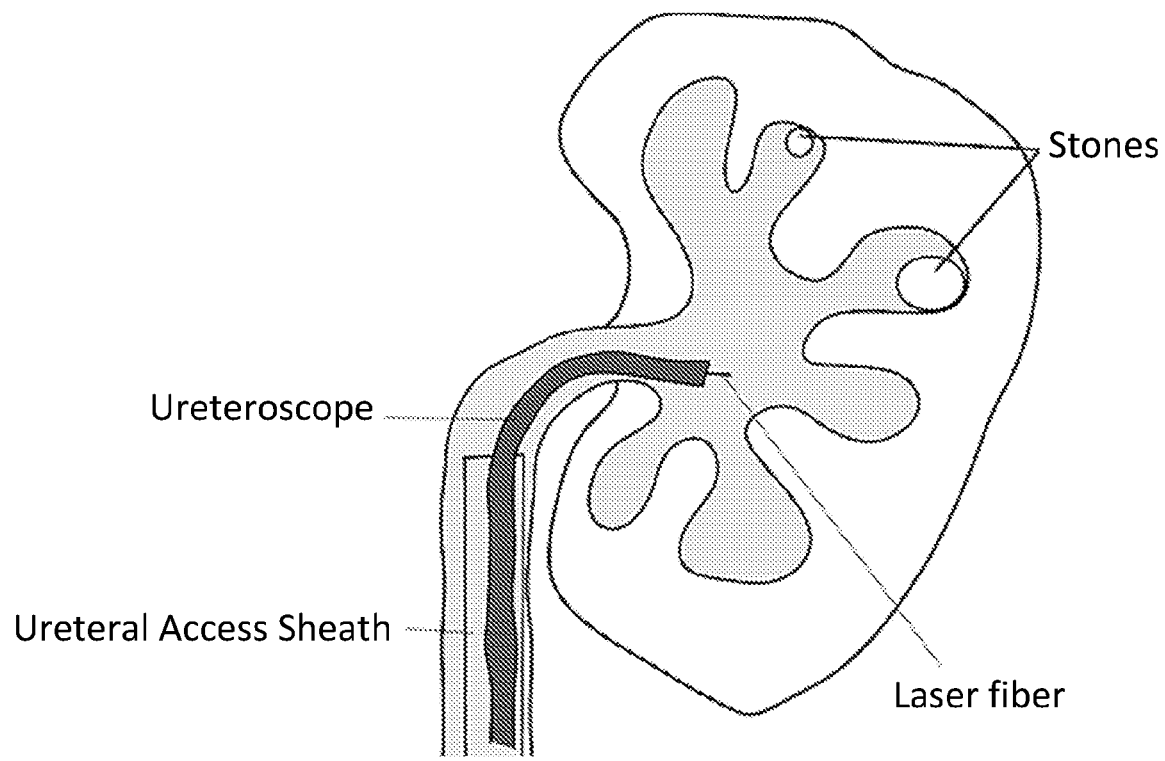
Figure 5:
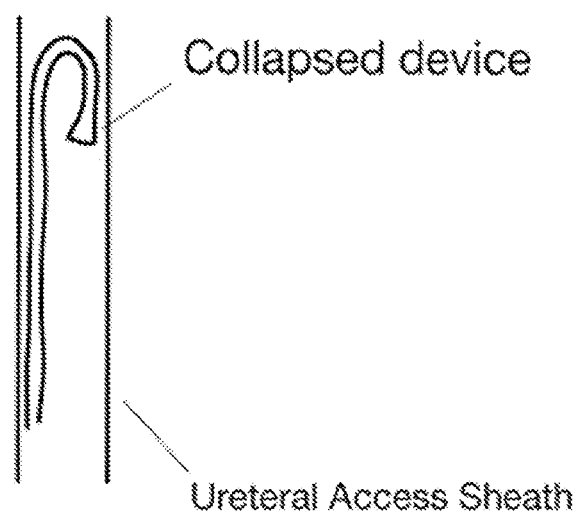
Figure 5:
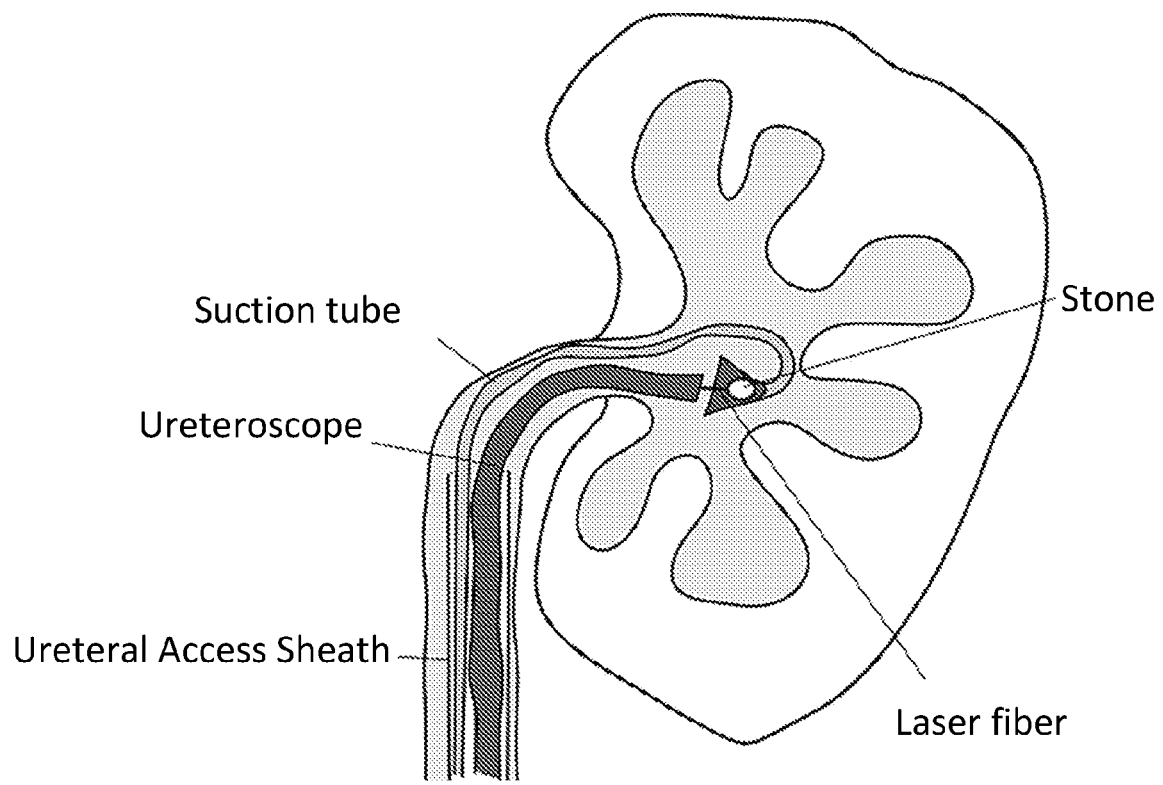

Now referring to FIGS. 5A-D, an exemplary method of using the described suction device is presented below. The present disclosure is not limited to the described method and specifically contemplates alternative methods of placing the device as described herein. In some embodiments, cystoscopy is performed with cannulation of the ureter and placement of a guidewire up the ureter to the renal pelvis. Next, as shown in FIG. 5A, over the guidewire, a conventional ureteral access sheath (e.g., 13/15 Fr) is placed with fluoroscopic guidance to the proximal ureter just below the ureteropelvic junction (UPJ) or into the renal pelvis if the UPJ will accommodate. The inner cannula is then removed, leaving the guidewire in place. Now referring to FIG. 5B, the ureteroscope is advanced into the renal pelvis and collecting system to survey the anatomy and localize stones. Large stones are fragmented with laser lithotripsy and collected in an upper or mid renal calyx. With ureteroscopic visualization, the guidewire is positioned with its tip located at the desired location of the suction cone and the ureteroscope is withdrawn leaving the guidewire in place. Now referring to FIG. 5C, the suction cone, in a collapsed or undeployed configuration, is advanced with the suction tubing through the access sheath to the renal pelvis. This is accomplished by placing the suction cone in the sheath with the suction tubing attached to the suction cone, advancing the suction cone over a guidewire, and pushing the suction cone to the renal pelvis with the flexible ureteroscope. In some embodiments, the suction cone is advanced by the surgeon up the ureter (through the access sheath) if the tubing is stiff enough to allow easy advancement without an additional "pusher." If the tubing is more flexible, the cone segment is pushed up the sheath using the ureteroscope as a pusher. The tubing from the cone passes alongside the ureteroscope down the sheath. In some embodiments where the suction tube is advanced over a guidewire, the guidewire is passed through an eyelet or channel on the suction cone as shown in FIG. 3B, and the guidewire does not pass through the suction tubing. With visualization from the ureteroscope, the suction cone is positioned in the desired position in the renal pelvis, upper pole calyx or mid pole calyx. The funnel of the suction cone is expanded with a suitable expansion mechanism (e.g., control wire). Once the suction cone is positioned and expanded, the suction pump is turned on. The ureteroscope is used to retrieve stone material using a conventional wire basket. Using the wire basket, the stone material is positioned within the cone. Once the cone has been "loaded" with one or more stones, the wire basket is removed and the laser fiber passed through the working channel of the ureteroscope. Now referring to FIG. 5D, the ureteroscope is advanced into the opening of the cone, and laser lithotripsy of the stone fragments is performed. Fluid continues to be infused into the collecting system through the working channel of the ureteroscope. Suction is applied via tubing from the tip of the suction cone, evacuating fluid, particulate material, and stone fragments up to 1 mm in size.

The suction serves to promote rapid flow of fluid from the ureteroscope through the cone and out of the body. This stabilizes stone material in the stone cone, minimizes retropulsion, and improves laser lithotripsy efficiency. This also improves visibility by clearing particulate material that would otherwise cloud the ureteroscopic field of view and provides a robust heat sink to prevent overheating of fluid in the collecting system and damage to the urothelium and renal tissue. Active suction extraction of stone fragments reduces residual stone burden and precludes the need to locate and manually extract residual stone fragments. After all stones have been treated with the suction cone, the cone is collapsed (e.g., using a control wire) and removed from the body. The ureteral access sheath (when used) is then removed with backloading of a guidewire, and ureteral stent placement is performed if indicated.

In some embodiments, the devices and systems described herein are used in combination with laser lithotripsy systems. The laser lithotripsy systems described herein further find use with additional ablation/fragmentation methods. Lasing may be performed with a pulsed high power Ho:YAG laser coupled to a fiber optic that can be passed through the working channel of a ureteroscope. The Ho:YAG laser may result in extremely high water absorption at the operating wavelength of 2100 nm, which decreases the effective penetration depth to no more than a few mm. This makes the device inherently safe, but also placing and maintaining the fiber tip close to the stone for effective treatment, generally less than 0.5 mm. A total of up to thousands of individual ablations (or pulses of energy) may be required for complete fragmentation of a stone, which can lead to lengthy procedures. After the surgeon has been able to subdivide the original stone(s) to a number of smaller fragments, a technique known as "popcorning" is sometimes used to quickly reduce fragments further to small enough size for passage. This is done by firing the laser at a high repetition rate within the center of a confined space allowing a turbulent mixing flow to develop. The fragments tumble within the flow randomly sometimes approaching the fiber tip where they are ablated. Because the fragments must be very close to the tip, a majority of pulses may be wasted, serving only to heat the fluid. There is a risk of heat damage to the kidney from pulsing even at moderate rates so it is helpful to minimize wasted pulses.

Figure 9:
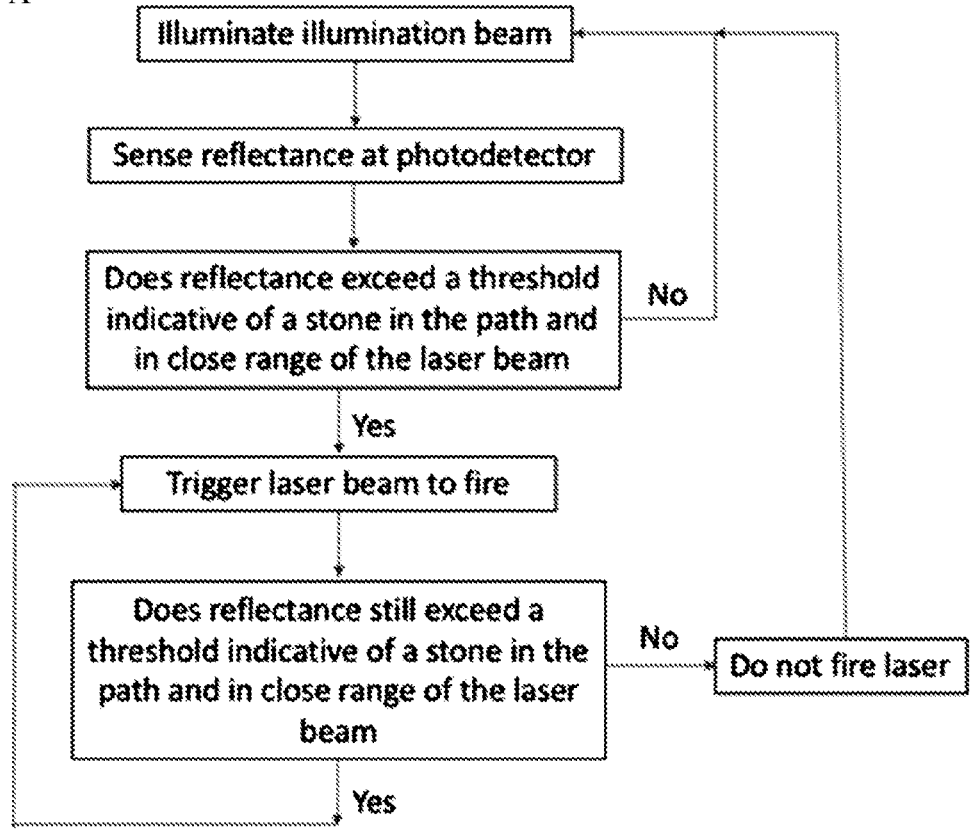
FIGS. 9A-B respectively show a A) flow chart of a laser sensing system and method; and B) schematic of the laser sensing system, according to an embodiment of this disclosure explained in Example 1 below.
Figure 9:
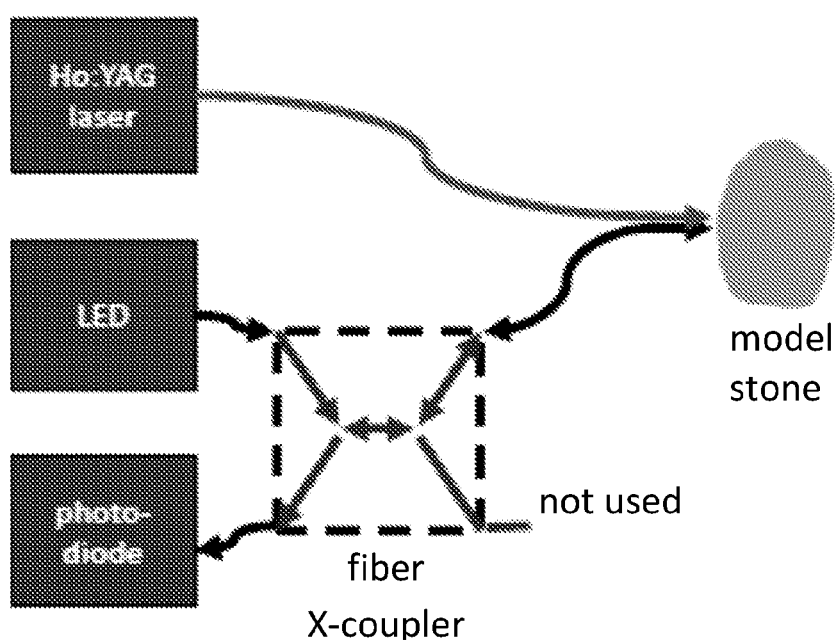

Accordingly, in some embodiments, provided herein are improved Ho:YAG laser systems and methods of operation. The improved laser systems and methods may be used in conjunction with the improved suction device or independently. FIG. 9A shows a flow chart of an exemplary process. Example 2 describes the system in use.

The Ho-YAG laser system described here includes a laser fiber and a sensing illumination beam from a low power (<10 mW) continuous or rapidly pulsed light source (FIG. 9A). In various embodiments, the laser fiber is the same or substantially similar to the laser fiber used in existing laser surgery systems. In some embodiments, the sensing beam is the visible aiming beam already present in existing laser surgery systems. In other embodiments, a supplemental light beam generator is provided. In some embodiments, the Ho-YAG laser system also includes a photodetector within the laser system. It has been found that the presence of a stone close to the end of a fiber increases light reflected back into the fiber. (See, e.g., Lange B, Jocham D, Brinkmann R, Cordes J. Stone/tissue differentiation during intracorporeal lithotripsy using diffuse white light reflectance spectroscopy: In vitro and clinical measurements. Lasers Surg Med. 2014 October; 46(8):614-9, and Lange B, Cordes J, Brinkmann R1. Stone/tissue differentiation for holmium laser lithotripsy using autofluorescence. Lasers Surg Med. 2015 November; 47(9):737-44, incorporated by reference in their entireties.) In embodiments of the present system, reflected light is detectable by a photodetector within the laser system. The photodetector is configured to sense the increased light reflectance from the presence of a stone. When the increased light reflectance indicative of a close-range stone is detected, the system is configured and programmed to trigger the Ho:YAG laser fiber to fire, maximizing ablation of the stone and eliminating wasted firings. This allows significantly more efficient use of laser pulses during "popcorning" as well as better ablation at lower rates.

In various embodiments, the laser system includes a computing module coupled to the photodetector and the laser fiber. The computing module includes a processor, for example, a general purpose microprocessor, which is coupled, via one or more buses, to memory in order to read information from, and optionally, write information to the memory. The memory may be any suitable computer-readable medium that stores computer-readable instructions for execution by computer-executable components. In various embodiments, the computer-readable instructions include software stored in a non-transitory format. The methods described below may be programmed as software instructions stored in the memory and executable by the processor.

In some embodiments, the laser system has various modes of firing. In one mode selectable by a user, the laser system is configured to fire automatically or semi-automatically at a high rate. Rather than firing at a constant rate, as is done in current systems, in the automatic or semi-automatic mode of embodiments of the present system, the laser only fires when a stone is detected to be in close range and in the path of the laser. In some embodiments, the laser system in this mode does not fire until a stone is in close range and in the path of the laser. Once such a stone is detected, the laser fires at a high rate until a stone is no longer detected to be in close range in the path of the laser. The laser pulse is then halted or delayed until a stone is again sensed to be in close range in the path of the laser. In some embodiments, the resulting pulse rate is variable and dependent on the surrounding environment.

In some embodiments, these systems and methods are used with a Thulium fiber laser, shorter wavelength IR lasers, or visible lasers.

EXAMPLES

The following examples are illustrative, but not limiting, of the devices, systems, and methods of the present invention. Other suitable modifications and adaptations of the variety of conditions and parameters normally encountered in clinical therapy and which are obvious to those skilled in the art are within the spirit and scope of the invention.

Example 1

Figure 7:
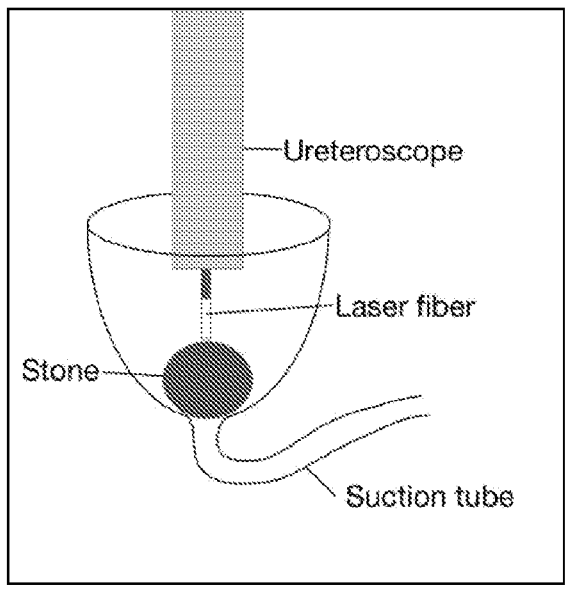
FIG. 7 shows a schematic of a model system used in Example 1, according to an embodiment of this disclosure.

Methods: Experiments were conducted in a tank of water with three spherical Begostones (3 mm diameter; composition: 15:5) contained within a prototype suction device or a simulated renal calyx (control). The suction device was conical in shape with a 1 mm opening at the bottom (FIG. 7) attached to tubing and a pump that provided suction to produce 120 mL/min flow rate. A 19 mm diameter vial was used to simulate a renal calyx. A flexible ureteroscope (DUR-8 Gyrus ACMI) containing a 242 µm laser fiber (Flexiva; Boston Scientific, MA) from a 120W holmium laser (P120; Lumenis, CA) was inserted into the test apparatus. Two laser settings could be used interchangeably, in particular 0.8 J×10 Hz (short pulse) and 0.5 J×80 Hz (short pulse), at the discretion of the operator during each trial. Each operator performed 5 trials with the simulated calyx and 5 trials with the suction device. Stone mass was recorded before and after each experiment. Time to complete treatment was recorded when less than 2 minutes. Statistical comparison was done by student's T test.

Results: The mean starting stone mass was 82 mg, (range 78 to 87 mg). Mean residual stone mass in the experimental group was 1 mg, (range 0 to 7 mg) and in the control group 29 mg (range 23 to 39 mg) representing a 1.9% residual mass in the experimental group and 36.0% residual mass in the control group (p value <0.001). These trends were consistent and statistically significant for both operators. In 6 of 10 trials in the experimental group, the stones were completely treated in less than two minutes (range 58 to 88 seconds).

Figure 8:
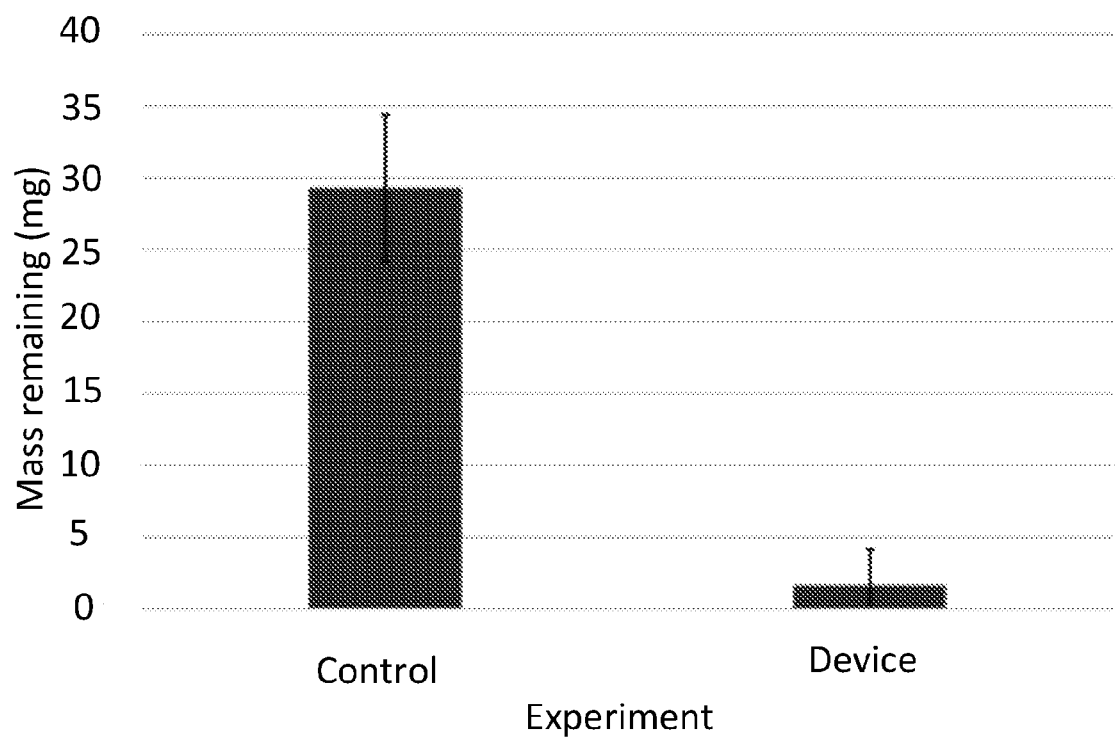
FIG. 8 is a graph of mean residual mass of stones remaining in a control group and a group using devices and methods of embodiments of this disclosure.

Conclusion: Confinement and suction stabilization of small stones improved efficiency of laser lithotripsy when compared with control trials. In 6 of 10 trials with this device, the stones were completely treated with no residual stone debris (FIG. 8).

Example 2

Effective and efficient ablation of stones by holmium laser lithotripsy requires the fiber tip to be in very close proximity to a stone. Achieving this can be difficult due to retropulsion from cavitation and the inability to precisely control the pulse timing on current laser systems. A set of three studies was performed to quantify this proximity effect and to show proof of concept for a laser system modification to improve laser lithotripsy efficiency. In part 1, the ablation volumes on model stones were measured at various fiber tip distances and laser power settings. In part 2, a method to continuously measure the distance from fiber tip to stone surface based on the reflectance of an aiming beam back into the fiber was developed. In part 3, distance was measured during a "pop dusting" scenario with rapidly moving stones to test the feasibility of detecting optimal firing times.

Methods: FIG. 9B shows an exemplary set up. Part 1: Flat plate model stones (Begostone) were treated with single laser firings per location at either 0.5 J or 1 J. Light was delivered by a 240 um laser fiber placed with a 3-axis positioner at various distances (0-3 mm) from the plate in a grid of locations. The volume of the craters formed was measured by reflectance microscopy. Part 2: Continuous light (<1 mW) from a 660 nm (red) LED was coupled into a 200 um fiber using a fiber X-coupler. Reflected light back into the fiber passed through the coupler to a biased photodiode and the resulting diode current was digitized by a PC oscilloscope. The fiber tip was placed at various distances (0-3 mm) from Begostone plates with a 3-axis positioner as in part 1. Normalized reflectance above baseline was recorded. Part 3: The LED fiber was taped immediately next to the holmium fiber and this pair was placed into a 3 mL round bottom test tube filled with water. Five spherical Begostones 3 mm in diameter were placed in the tube. The laser was fired at 40 Hz, 0.5 J for 1 minute while recording light reflectance on the second fiber.

Figure 10:
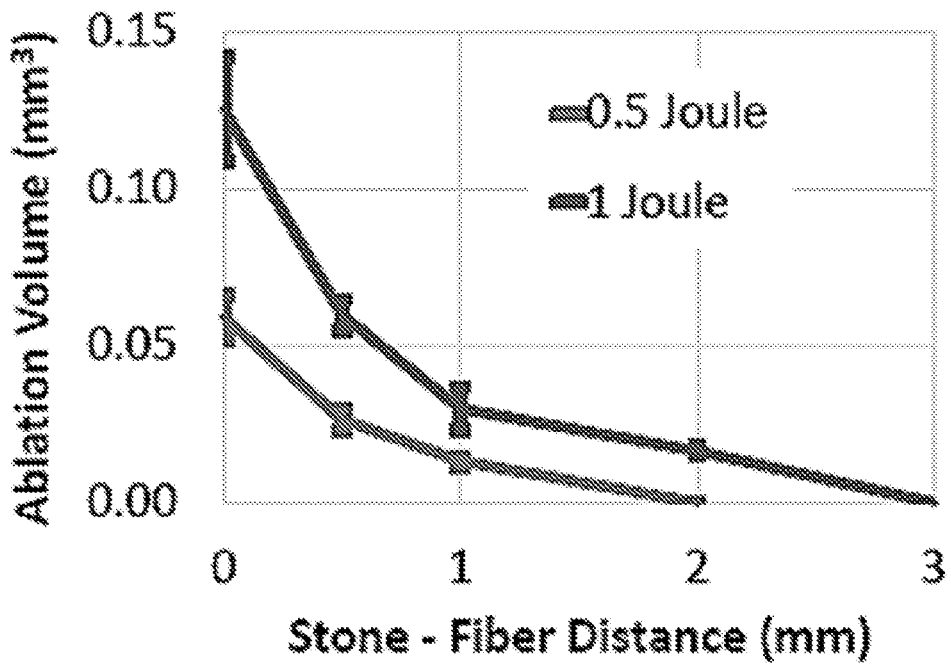
FIGS. 10A-C respectively show A) a graph of stone-fiber distance vs. ablation volume; B) a graph of stone-fiber distance vs. reflectance change: and C) images of ablated stones, as explained in Example 2 below.
Figure 10:
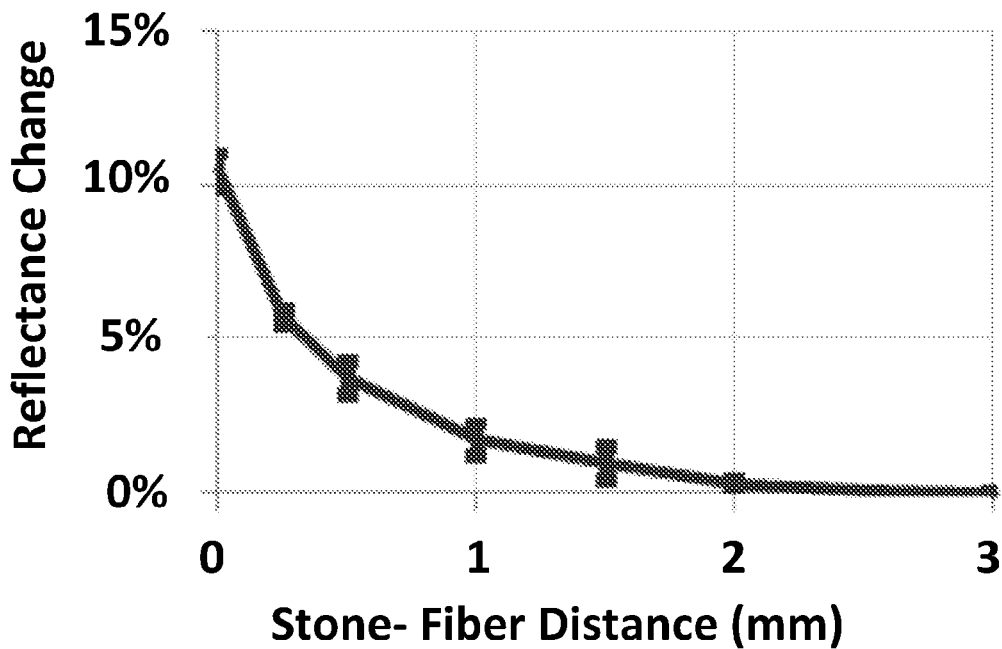
Figure 10:
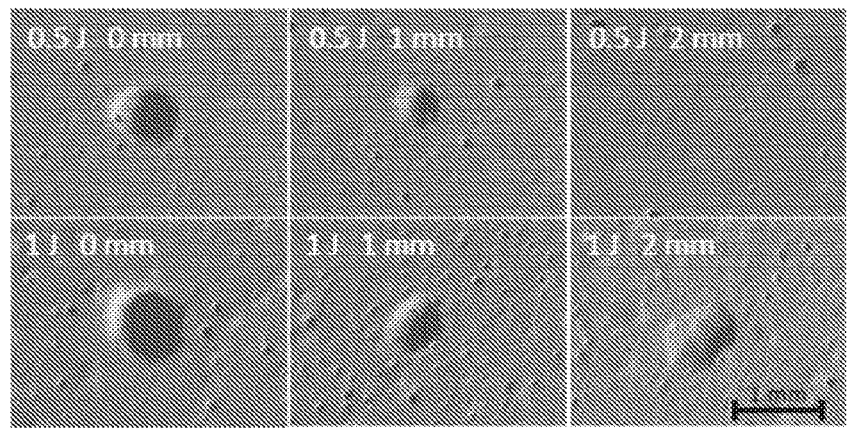
Figure 11:
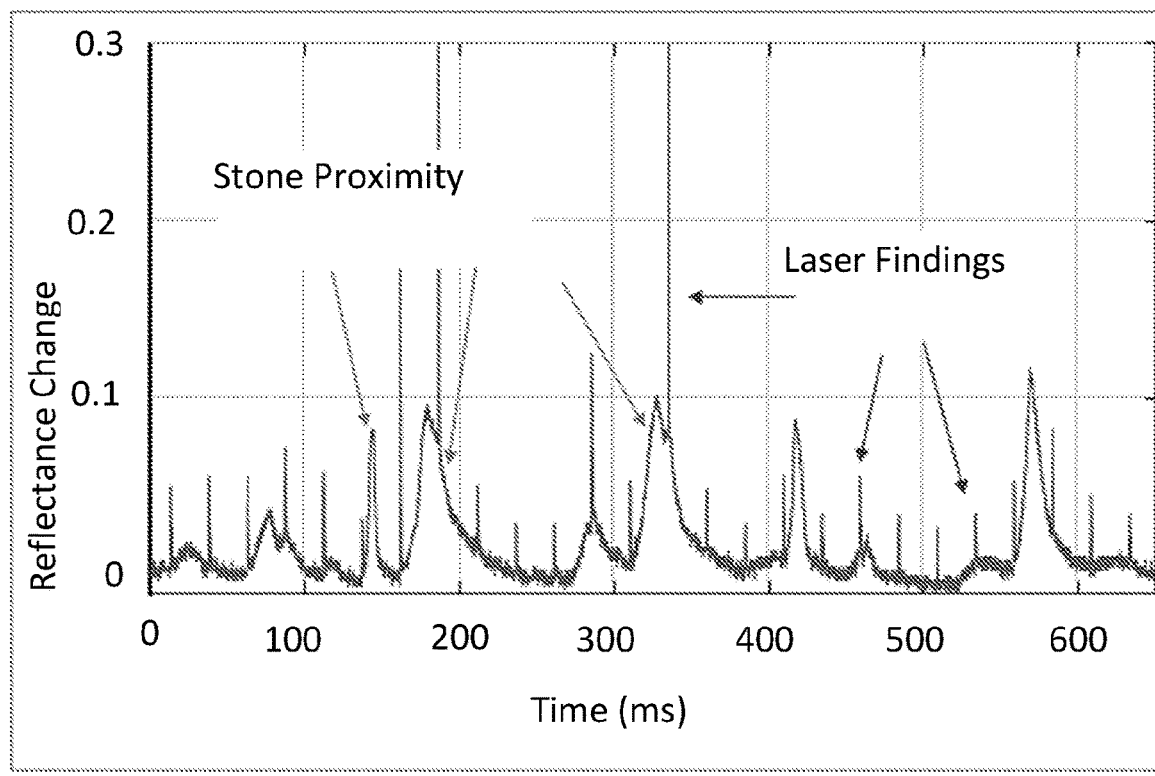
Figure 11:
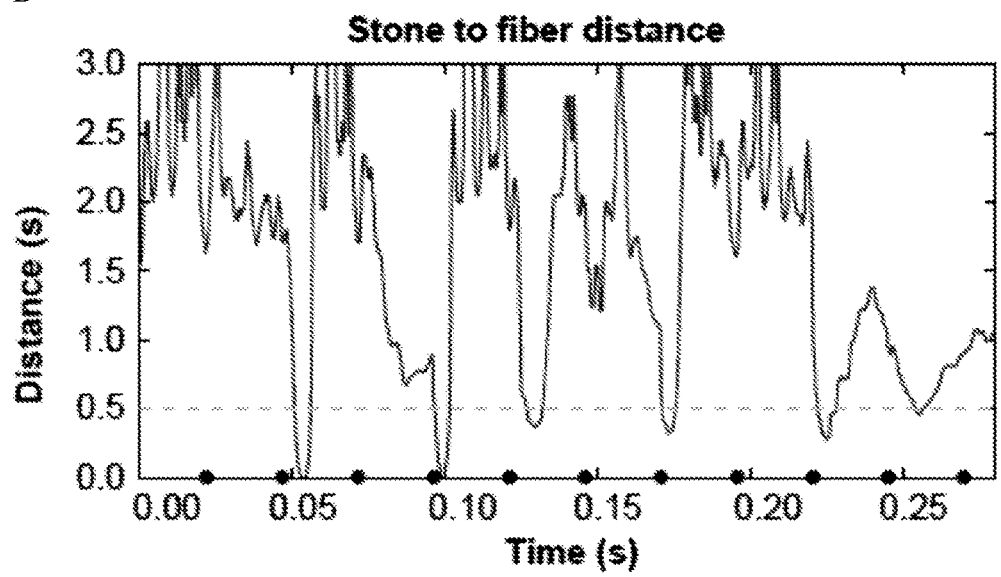

Results: Part 1: The volume of ablated material declined rapidly as the fiber to stone distance increased (FIGS. 10A and C). Even at 0.5 mm, the ablation volume was significantly lower than at 0. Part 2: The reflectance increased exponentially beginning at a stone to fiber distance of 2 mm reaching about 10% at 0 (FIG. 10B). Part 3: Pulses from the holmium laser showed as sub-millisecond spikes in the reflectance (FIG. 11A-B). A slower variation in the reflectance (10 s milliseconds) corresponded to the proximity of a stone. The vast majority of laser pulses did not occur during the brief periods when a stone was in close proximity (<0.5 mm) to the fiber.

Conclusion: This work shows the inefficiency of fixed firing rates for holmium laser lithotripsy and describes a simple stone proximity sensing system that is, in some embodiments, incorporated into a laser system to control the precise timing of laser firings for significantly higher efficiency.

All publications and patents mentioned in the above specification are herein incorporated by reference as if expressly set forth herein. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in relevant fields are intended to be within the scope of the following claims.

The invention claimed is:

1. A device, comprising:
   suction tubing having or configured to have a bend of greater than 90 degrees in a distal portion of the suction tubing; and
   a suction cone comprising an opening at a proximal end, wherein said proximal opening has a diameter of 0.5 to 1.5 mm and comprises a rounded proximal region adjacent said proximal opening, wherein said proximal region has a smaller outer diameter than said suction cone, and wherein said opening is operably linked to the suction tubing and a suction cone body comprising a distal opening, wherein said distal opening has a larger diameter than said proximal opening, and wherein said distal opening has a diameter of 4-12 mm, wherein said suction cone comprises a wire wrapped around said suction cone that controls deployment of said wire between a collapsed configuration and an expanded configuration, and
   wherein said suction tube is deployable between a collapsed configuration and an expanded configuration and further comprises one or more wires configured for deploying the suction tubing into the expanded configuration, and wherein when said device is in said expanded configuration, said suction tubing is oriented in a curved configuration.

2. The device of claim 1, wherein said suction cone is constructed of a flexible material selected from the group consisting of a polymer, nickel titanium, and a wire mesh.

3. The device of claim 1, wherein said suction tubing extends from said proximal opening of said suction cone and makes a turn greater than 90 degrees when said suction cone is in a deployed configuration.

4. A system, comprising:
   the device of claim 1; and
   a suction pump.

5. The system of claim 4, wherein said system further comprises one or more of a ureteroscope and a laser fiber.

* * * * *